(12) United States Patent
Barnikow et al.

(10) Patent No.: US 9,109,527 B2
(45) Date of Patent: Aug. 18, 2015

(54) DEVICE AND METHOD FOR DIAGNOSING AN EXHAUST GAS SENSOR

(75) Inventors: Stefan Barnikow, Munich (DE); Frank Friedhof, Regensburg (DE); Ekkehart-Peter Wagner, Bad Abbach (DE)

(73) Assignee: Continental Automotive GmbH, Hannover (DE)

( * ) Notice: Subject to any disclaimer, the term of this patent is extended or adjusted under 35 U.S.C. 154(b) by 590 days.

(21) Appl. No.: 13/503,507

(22) PCT Filed: Oct. 14, 2010

(86) PCT No.: PCT/EP2010/065397
§ 371 (c)(1),
(2), (4) Date: Jun. 12, 2012

(87) PCT Pub. No.: WO2011/048002
PCT Pub. Date: Apr. 28, 2011

(65) Prior Publication Data
US 2012/0266647 A1 Oct. 25, 2012

(30) Foreign Application Priority Data
Oct. 22, 2009 (DE) .......... 10 2009 050 221

(51) Int. Cl.
*G01N 37/00* (2006.01)
*F02D 41/14* (2006.01)
*G01N 27/419* (2006.01)
(Continued)

(52) U.S. Cl.
CPC ........ *F02D 41/1495* (2013.01); *F02D 41/1477* (2013.01); *G01N 27/419* (2013.01); *F02D 41/1454* (2013.01); *F02D 41/1456* (2013.01); *F02D 41/222* (2013.01); *F02D 2041/2089* (2013.01); *F02D 2041/2093* (2013.01)

(58) Field of Classification Search
CPC ........................... G01N 33/0006; G01N 27/30
USPC ................................... 73/1.06, 23.2
See application file for complete search history.

(56) References Cited

U.S. PATENT DOCUMENTS

| | | |
|---|---|---|
| 6,120,663 A | 9/2000 | Kato et al. |
| 6,266,993 B1 | 7/2001 | Diehl et al. |
| 6,763,697 B2 | 7/2004 | Bolz |

(Continued)

FOREIGN PATENT DOCUMENTS

| | | |
|---|---|---|
| DE | 19845927 A1 | 4/2000 |
| DE | 10029831 C1 | 2/2002 |

(Continued)

*Primary Examiner* — Hezron E Williams
*Assistant Examiner* — Mark A Shabman
(74) *Attorney, Agent, or Firm* — Laurence A. Greenberg; Werner H. Stemer; Ralph E. Locher

(57) ABSTRACT

A device for diagnosing an exhaust gas sensor, in particular a linear oxygen probe, for an internal combustion engine. A diagnostic unit is configured to control a first and a second current source in a coordinated manner in order to generate a first and a second current. Each of the currents has a predefined polarity sign, and is designed to determine the first and/or second and/or third voltages applied at a first and/or second and/or third terminal when first and second currents flow and put the amounts of the voltages in relation to the coordinated currents such that line interruptions and/or short circuits can be detected at the first and/or second and/or third terminal.

14 Claims, 8 Drawing Sheets

(51) Int. Cl.
  *F02D 41/22* (2006.01)
  *F02D 41/20* (2006.01)

(56) References Cited

U.S. PATENT DOCUMENTS

| 7,073,320 | B2 | 7/2006 | Moritsugu et al. | |
|---|---|---|---|---|
| 7,142,976 | B2 * | 11/2006 | Inoue et al. | 701/114 |
| 7,427,347 | B2 | 9/2008 | Bausewein et al. | |
| 2002/0175086 | A1 | 11/2002 | Nakamichi et al. | |
| 2004/0221641 | A1 | 11/2004 | Moritsugu et al. | |
| 2009/0299601 | A1 | 12/2009 | Kunihiro | |
| 2012/0167656 | A1 * | 7/2012 | Verdier et al. | 73/1.06 |

FOREIGN PATENT DOCUMENTS

| DE | 69802340 | T2 | 7/2002 |
|---|---|---|---|
| EP | 1460417 | A1 | 9/2004 |
| EP | 1480039 | A1 | 11/2004 |
| WO | 2008058832 | A1 | 5/2008 |

* cited by examiner

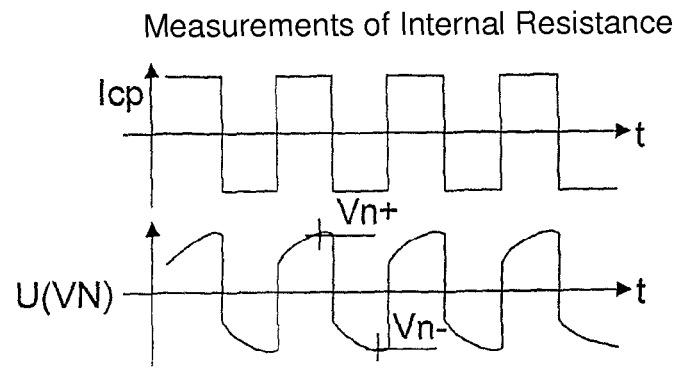
FIG. 8A
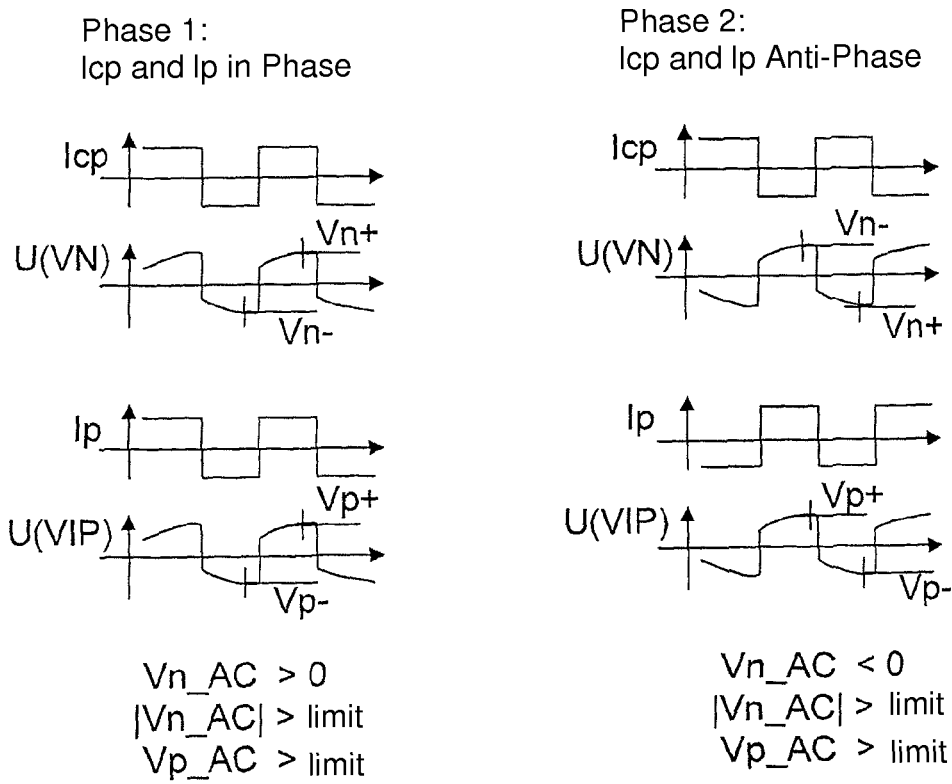
FIG. 8B
FIG. 8C

DEVICE AND METHOD FOR DIAGNOSING AN EXHAUST GAS SENSOR

BACKGROUND OF THE INVENTION

Field of the Invention

The invention relates to a device and a method for diagnosing an exhaust-gas sensor, in particular a linear oxygen probe, for an internal combustion engine.

When internal combustion engines operate, exhaust-gas sensors whose signal is used to control the emissions of the internal combustion engines are employed to permit compliance with legally specified emission limiting values. Frequently employed exhaust-gas sensors are what are referred to as binary and linear lambda sensors as well as NOx sensors. These types of exhaust-gas sensors each comprise a heated solid electrolyte composed of yttrium-stabilized zirconium dioxide ceramic ($ZrO_2$). In order to be able to measure the oxygen concentration or NOx concentration in the form of an oxygen ion stream through the solid electrolyte in exhaust-gas sensors which are composed of zirconium dioxide, there is provision for the ceramic to be heated. The target temperature is either regulated to a predefined value or pilot-controlled as a function of the operating point.

The basic material zirconium dioxide has two essential properties:

1. If an oxygen concentration of lambda=1 is present at one electrode of the exhaust-gas sensor and an oxygen concentration of lambda=infinite (equivalent to the surrounding air) is present at another electrode of the exhaust-gas sensor, an electrical voltage of 450 mV occurs between the two electrodes. This voltage is referred to as a Nernst voltage, which is named after the physician Walther Nernst.
2. If an electric current is conducted through the zirconium dioxide of the exhaust-gas sensor, oxygen particles are transported through the zirconium dioxide.

A widespread design of linear exhaust-gas sensors is composed of an arrangement of two cells of the basic materials zirconium dioxide which are connected to one another. In one of the cells, referred to as Nernst cell, the property specified under 1. here is utilized. In the other, second cell, which is referred to as the pump cell, the property which is referred to above under 2. is utilized. Located between the two cells in such a linear exhaust-gas sensor is an enclosed cell (referred to as the reference cavity), which is connected to the exhaust gas stream through a diffusion barrier and in which an oxygen concentration of lambda=1 is intended to occur. As long as the oxygen concentration has the value lambda=1, an electrical voltage of 450 mV can be measured between the electrodes of the Nernst cell. However, as soon as oxygen particles flow in or out through the diffusion barrier as a result of a deviation from the ideal oxygen concentration $\lambda=1$ in the exhaust gas, the oxygen concentration in the enclosed cell is affected. As a result, the electrical voltage between the electrodes of the Nernst cell differs from the 450 mV which is to be achieved.

An electronic control system or actuation device which is connected to the exhaust-gas sensor has the function of measuring the voltage value across the Nernst cell which differs from the 450 mV and of initiating a suitable counter-reaction in order to restore the voltage of 450 mV. The counterreaction consists in feeding an electric current through the pump cell of the exhaust-gas sensor. As a result, so many oxygen particles are transported into the enclosed cell that the oxygen concentration is equalized again to lambda=1. The flow of current can occur in both directions here since the oxygen concentration in the exhaust gas can be higher as well as lower than lambda=1.

In terms of control technology, the exhaust-gas sensor therefore constitutes a controlled system which has to be held at the working point by the connected actuation device.

In exhaust-gas sensors, in particular in linear oxygen probes, the temperature of the ceramic material is controlled precisely since the measuring accuracy of the exhaust-gas sensors is dependent to a considerable degree on the temperature. A current method for measuring temperature consists in using an alternating-current signal which is temporarily or continuously connected to the sensor cells and temporarily or continuously evaluated. In this context, the resulting oscillating voltage drop across the probe cell is measured. The acquired cell impedance constitutes an indirect measure of the temperature of the corresponding cell. In order to carry out the impedance measurement, in linear exhaust-gas sensors the regulation of the cell voltage 450 mV is generally maintained for a specific time in order to determine the resulting oscillating voltage signal in this time period. Alternatively, an alternating-voltage signal is superimposed on the direct-voltage-oriented Nernst cell signal and the direct voltage signal which is necessary to regulate the Nernst voltage is disconnected from the alternating-voltage signal necessary for regulating the temperature, by means of a suitable analog filter circuit.

In order to meet legal requirements, it is also necessary to test the electrical terminals of the exhaust-gas sensor for short circuits and breaks. Short circuits can be detected at respective terminals of the exhaust sensor by comparing the voltage present there with predefined upper or lower limits. The detection of breaks is correspondingly difficult and has previously been implemented by means of costly plausibility testing performed on the output signals of the actuation circuit for the exhaust-gas sensor. Line breaks can be detected, for example, on the basis of measured internal resistances and pumping currents or on the basis of the behavior of control loops which are based thereon, under suitable operating conditions of the engine.

BRIEF SUMMARY OF THE INVENTION

The object of the present invention is to specify a device and a method with which faults can be more easily detected.

These objects are achieved by means of a device according to the features of patent claim 1 and a method according to the features of patent claim 14. Advantageous refinements emerge from the dependent patent claims.

The invention provides a device for diagnosing an exhaust-gas sensor, in particular a linear oxygen probe, for an internal combustion engine. The device comprises a first terminal for connecting to a first electrode of a first said of the exhaust-gas sensor, a second terminal for connecting to a second electrode of a second cell of the exhaust-gas sensor, a third terminal for connecting to a node of a second electrode of the first cell and a first electrode of the second cell of the exhaust-gas sensor. In a linear exhaust-gas sensor, the first cell is referred to as a Nernst cell. The second cell constitutes what is referred to as the pump cell. The device also comprises a first power source which is coupled to the first terminal in order to generate a current and to apply the first current to the first cell, and a second power source which is coupled to the second terminal in order to generate a second current and to apply the second current to the second cell. The third terminal is held at a specific, constant or variable, voltage, for example by connecting said voltage to a voltage source or to ground.

The device according to the invention is distinguished by a diagnostic means which is designed to control the first and the second power source in a coordinated fashion in order to generate the first and the second current with respectively predefined signs, and to determine the first and/or second and/or third voltages when the respective first and second currents are present at the first and/or second and/or third terminal and to relate the absolute values thereof to the coordinated currents, as a result of which line breaks and/or short circuits at the first and/or second and/or third terminal can be detected.

The invention also relates to a method for diagnosing an exhaust-gas sensor, in particular a linear oxygen probe, for an internal combustion engine by means of a device of the type described above. In the method according to the invention, the first and the second power source are controlled in a coordinated fashion in order to generate the first and the second current with respectively predefined signs. The first and/or second and/or third voltages when the respective first and second currents are present at the first and/or second and/or third terminal are determined and the absolute values thereof are related to the coordinated currents in order to detect line breaks and/or short circuits at the first and/or second and/or third terminal.

The invention permits, in particular, the detection of line breaks without additional function units in an actuation circuit which actuates the exhaust-gas sensor. If the exhaust-gas sensor is embodied as a linear oxygen probe, an alternating-current power source is provided for the Nernst cell for the measurement of the internal resistance. A further power source is necessary for the pump cell for the generation of a pumping current. The two power sources can be employed for the diagnostics according to the invention, i.e. the coordinated generation of power by virtue of the fact that these diagnostic means which are provided according to the invention are actuated in a predefined, coordinated fashion. The diagnosis of the exhaust-gas sensor can be carried out very quickly. Furthermore, it is possible to detect symptoms which indicate a line fault and which make actuation of the diagnostics necessary. A further advantage is that this requires less time than the legal limit.

The invention is based on the realization of the behavior of real power sources. A real power source can drive its nominal current only if the voltage at the output of the power source is within a specific range. The current typically decreases and increases when the voltage approaches one of the supply voltages of the power source. If a resistor is connected to the output of the power source and if the resistance is too large, the output voltage of the power source drops or rises in the direction of one of the supply voltages of the power source, wherein the absolute value of the current becomes small. If a positive and then a negative current are set at the power source, a high and a low output voltage respectively occur when there is a high voltage or respectively an infinite voltage, with a positive voltage resulting in the case of a positive current, and a negative voltage resulting in the case of a negative current. Taking into account this realization of the behavior of real power sources permits breaks in lines to be detected. In order to be able to be determine in which of the lines which are connected to the first, second or third terminal of the device to be diagnosed a break is present, the control of the first and second power source is carried out in a coordinated fashion and the voltages which are present at the respective terminals are evaluated.

The detection of a break in a line which is connected to the third terminal is of particular interest. The return lines of the first and second cells are usually combined by means of the third terminal and connected, in the actuation circuit or diagnostic circuit, to what is referred to as a "virtual ground" which is a voltage source in terms of its current/voltage characteristic.

According to the invention, in order to detect a line break at the third terminal, the diagnostic means is designed (a) to detect the voltages at the first and the second terminal when there is a positive first current and a positive second current, (b) to detect the voltages at the first and the second terminal when there is a negative first current and a negative second current, (c) to detect the voltages at the first and the second terminal when there is a positive first current and a negative second current, and (d) to detect the voltages at the first and the second terminal when there is a negative first current and a positive second current.

In particular, in order to detect a line break at the third terminal, the diagnostic means is designed to generate in the case of (c) the first current with an absolute value smaller than the second current, and in the case of (d) the first current with an absolute value smaller than the second current. The principle can, however, likewise be applied if in these cases the first current is larger in absolute terms than the second current.

In a further specific example, in order to detect a line break at the third terminal, the diagnostic means is designed, in the case of (a) to detect the high voltage at the first terminal and the second terminal, respectively, and in the case of (b) to detect a low voltage at the first terminal and the second terminal, respectively, and in the case of (c) to detect a low voltage at the first terminal and the second terminal, respectively, and in the case of (d) to detect a high voltage at the first terminal and the second terminal, respectively. A high voltage is understood here to be a voltage which is close to the upper supply voltage of the respective power source. The low voltage is understood to be a voltage which is close to the lower supply voltage of the respective power source. This is based on the fact that the first and second currents cannot flow via the third terminal, and the sum of the first and the second current therefore has to be zero. Here, in the cases (a) and (b) the voltages at the first and second terminals do not differ significantly from those which occur when there is a break in the actual lines which are connected to the respective terminals. However, in cases (c) and (d) the behavior at the terminal with a lower set current in absolute terms is different. Where a high voltage is to be expected when there is a break in the line at the first terminal itself, a low voltage is observed, and vice versa.

According to a further expedient refinement, during the generation of the first and/or second currents, an exhaust-gas measurement is interrupted by the diagnostic means in order to determine a line break and/or a short circuit. The diagnostics require specific currents to be applied to the first and second cell of the exhaust-gas sensor. The diagnostics therefore require the normally active pumping current control (in the case of a linear exhaust-gas probe) to be switched off. No lambda measurement can be performed during this time.

However, the interruption in the lambda measurement is generally not critical since the presence of a line fault as a matter of principle gives rise to typical symptoms. For example, an excessively high resistance is measured or the pumping current controller runs up against a limit. There is expediently provision for the diagnostic means to be activated only if a fault detection means has detected the presence of a fault at the exhaust-gas sensor. The diagnostic means ultimately serve to locate the fault precisely.

According to a further refinement, the diagnostic means comprises a first signal filter which is connected to the first and third terminal and by means of which a first amplitude, resulting from the first current, of the cell voltage of the first cell can be determined, and/or which is connected to the second and third terminal and by means of which a second amplitude, resulting from the second current, of the cell voltage of the second cell can be determined. The first signal filter can expediently be switched between the first and third terminal and the second and third terminal.

In particular, the diagnostic means comprises a first computing unit for determining a mean value of the cell voltage of the first cell. This refinement is particularly expedient if an internal resistance measurement is implemented in the actuation circuit for the exhaust-gas sensor and the results thereof can be used. The internal resistance measurement applies an alternating current to the first cell (to the Nernst cell in the case of a linear exhaust-gas probe). This means that positive and negative first currents are generated by the internal resistance measurement. The signal filter which is coupled to the first and the third terminal determines the resulting amplitude of the Nernst cell voltage. This means that the amplitude results from the difference between the voltages on the first line, which voltages occur when there is a positive and a negative first current. The signal filter continues to determine the mean value of the Nernst cell voltage.

In a corresponding way, the diagnostic means comprises a second signal filter which is connected to the second and third terminal and by means of which a second amplitude, resulting from the second current, of the cell voltage of the second cell can be determined. In particular, the diagnostic means comprises a second computing unit for determining a mean value of the cell voltage of the second cell. The use of a single signal filter, which can be optionally connected to the first or the second terminal, is particularly advantageous. Providing a respective signal filter, which is assigned to the first or second cell, and the possibility of being able to determine amplitude mean values of the respective cell voltages in the case of in phase and anti-phase first and second currents, permits a multiplicity of electrical faults to be detected. In particular, the following faults can be detected:
  no fault
  the line which is connected to the first terminal is interrupted, wherein the state of the line which is connected to the third terminal cannot be detected,
  the line which is connected to the second terminal is interrupted, wherein the state of the line which is connected to the third terminal cannot be detected,
  the lines which are respectively connected to the first and the second terminals are interrupted, wherein the state of the line which is connected to the third terminal cannot be detected,
  the line which is connected to the third terminal is interrupted, wherein the lines which are connected to the first and second terminal are satisfactory,
  there is a short circuit with an upper supply voltage on the first line
  there is a short circuit with a lower supply voltage at the first terminal,
  there is a short circuit with the upper supply voltage at the second terminal,
  there is a short circuit with the lower supply voltage at the second terminal,
  there is a short circuit with the upper supply voltage at the third terminal, and
  there is a short circuit with the lower supply voltage at the third terminal.

According to a further specific refinement, the first power source is an alternating current power source for measuring an internal resistance of the first cell. It is also expedient if the second power source is a pumping power source or is embodied as a separate power source. If these two features are present, no further elements are necessary to determine the amplitudes and the mean value since the respective values are required for the measurement and the internal resistance of a linear exhaust-gas probe.

The invention will be explained in more detail below with reference to the figures, in which:

BRIEF DESCRIPTION OF THE SEVERAL VIEWS OF THE DRAWING

FIG. 8a shows a schematic illustration of the measurement of the internal resistance which is carried out at a linear oxygen probe, and FIGS. 8b and 8c show the use of the measurement of the internal resistance for troubleshooting.

DESCRIPTION OF THE INVENTION

Figure 1:
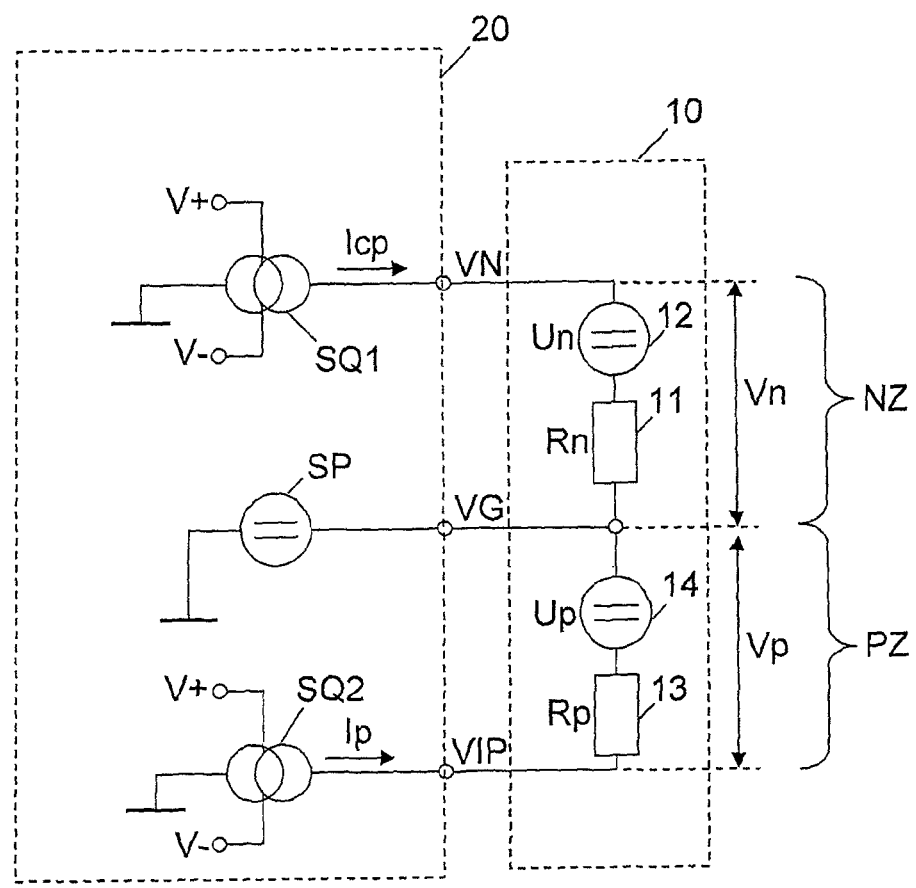
FIG. 1 shows a circuit arrangement which shows the basic actuation of a linear oxygen probe, FIG. 2a, b, c show the current/voltage characteristic of a real power source, FIG. 3a, b, c show the behavior of the current and voltage of a real power source to which a high output resistance is connected, FIG. 4a, b show an equivalent circuit diagram and the profile of the voltage at the second terminal of a diagnostic circuit according to the invention in the case of positive first and second currents and a line break at the third terminal of the diagnostic circuit, FIG. 5a, b show an equivalent circuit and the profile of the voltage at the second terminal of the diagnostic circuit according to the invention in the case of a positive first and a negative second current and a line break at the third terminal of the diagnostic circuit, FIG. 6a, b show an equivalent circuit diagram and the profile of the voltage at the second terminal of the diagnostic circuit according to the invention in the case of a negative first and a positive second current and a line break at the third terminal of the diagnostic circuit.

FIG. 1 shows an electrical equivalent circuit diagram of an exhaust-gas sensor 10 which is embodied as a two-cell pumping current probe which is regulated and monitored by an actuation circuit 20.

Only the parts which are relevant to the invention are respectively illustrated here.

The exhaust-gas sensor 10 comprises, in a known fashion, a Nernst cell NZ as a first cell and a pumping cell PZ as a second cell. The electrical equivalent circuit diagram of the Nernst cell NZ is formed by the series circuit composed of a resistor 11 with the resistance value Rn and a voltage source 12 with the Nernst voltage Un. In a corresponding way, the electrical equivalent circuit diagram of the pumping cell PZ is formed by the series circuit composed of a resistor 13 with the resistance value Rp and a voltage source 14 with a pumping voltage Up. The Nernst cell NZ and the pumping cell PZ are in turn connected to one another in a serial fashion, wherein a Nernst cell voltage Vn drops across the Nernst cell NZ, and a pumping cell voltage Vp drops across the pumping cell PZ.

The Nernst cell is connected between the first terminal VN and the third terminal VG of the actuation circuit 20. The pumping cell PZ is connected between a second terminal VIP and the third terminal VG of the actuation circuit. Accordingly, the node between the pump cell PZ and the Nernst cell NZ is connected to the third terminal VG. In reality, respective electrodes of the Nernst cell NZ and the pumping cell PZ are connected to the first, the second and the third terminal VN, VIP, VG, wherein what is referred to as a return line of the exhaust-gas sensor 10 is connected to the terminal VG.

The actuation circuit 20 comprises a first power source SQ1, which is embodied as an alternating current power source. The alternating power source SQ1 serves to measure the internal resistance of the Nernst cell NZ and is connected for this purpose to the first terminal VN. Said alternating-current power source is operated with a positive supply voltage V+ and a negative supply voltage V−.

A first current Icp, generated by the first power source SQ1, has a positive absolute value in the present description if said current Icp flows in the direction of the arrow from the first power source SQ1 in the direction of the Nernst cell NZ. In a corresponding way, the first current Icp flows with the negative absolute value from the Nernst cell NZ in the direction of the first power source SQ1.

The actuation circuit 20 also comprises the second power source SQ2 which serves to generate a pumping current of the pumping cell PZ. The second power source SQ2 is connected to the second terminal VIP, wherein a current Ip which is positive in absolute terms flows from the second power source SQ2 in the direction of the pumping cell PZ (with the direction of the arrow shown in the figure). A second current which is negative in absolute terms flows from the pumping cell PZ via the second terminal VIP in the direction of the second power source SQ2.

The third terminal VG which is connected to the return lines of the Nernst cell NZ and of the pumping cell PZ is connected at the actuation circuit 20 to what is referred to as a "virtual ground" which is a voltage source SP in terms of the current/voltage characteristic.

The current/voltage characteristics of the first and second power sources SQ1, SQ2 and of the virtual ground which is embodied as a voltage source SP are utilized for the procedure according to the invention.

Figure 2A:
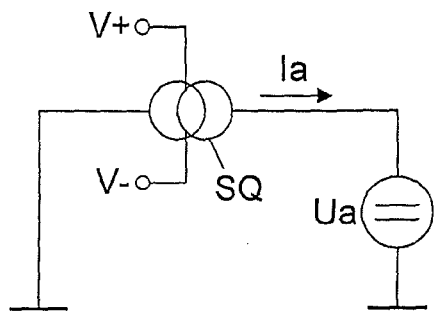
Figure 2B:
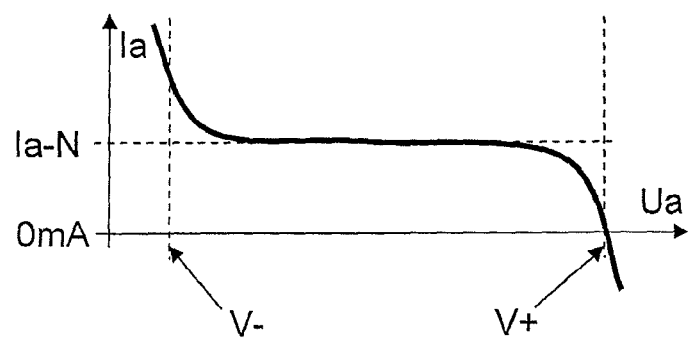
Figure 2C:
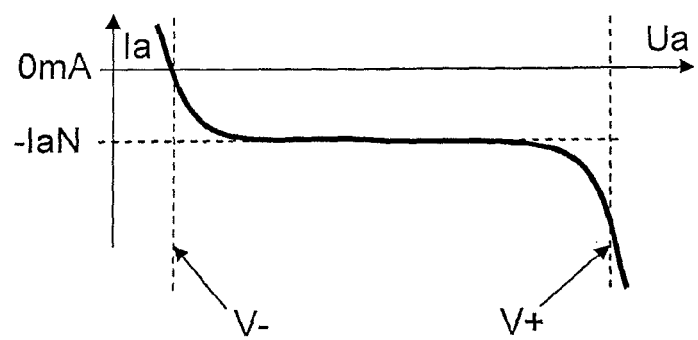

A real power source can drive its nominal current only if the voltage at its output lies within a specific range. Typically, the voltage decreases and respectively increases if the voltage lies one of the supply voltages V+, V− of the voltage source. This is illustrated by way of example in FIG. 2. In this case, FIG. 2a shows the electrical equivalent circuit diagram of a real power source SQ which is supplied by supply voltages V+, V−. On the output side, the real power source SQ is coupled to a voltage source Ua, wherein the power source SQ drives a current Ia in the direction of the voltage source Ua. FIGS. 2b and 2c each illustrate the characteristic of the current Ia as a function of the voltage Ua. In this case, FIG. 2b shows the characteristic for a positive rated current (i.e. the current Ia flows in the direction characterized by an arrow in FIG. 2a), while FIG. 2c illustrates the characteristic for a negative rated current. It is clearly apparent here that the current Ia corresponds to a rated current Ia_N and respectively −Ia_N as long as the voltage Ua does not approach the lower or upper supply voltage V−, V+.

Figure 3A:
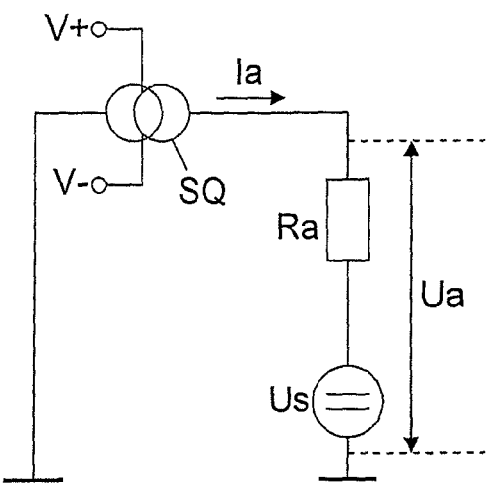
Figure 3B:
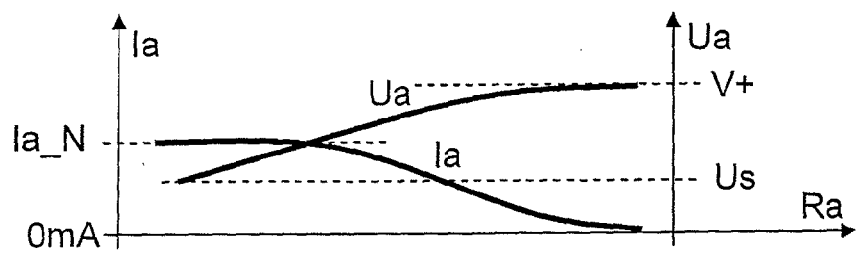
Figure 3C:
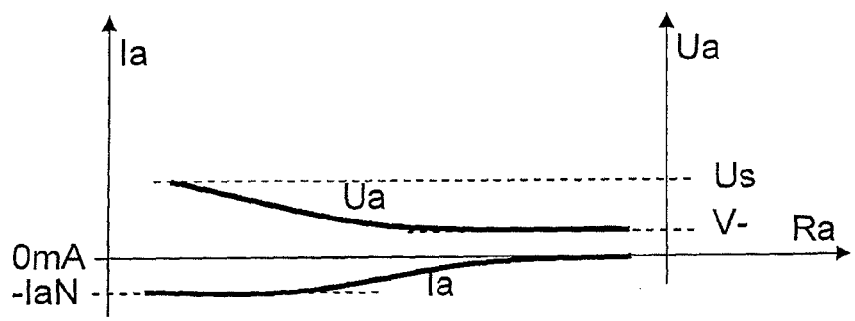

FIG. 3 shows the case in which the power source SQ must drive its current Ia through a very high resistance Ra, which is infinite in a borderline case. If the resistance Ra is too large, the output voltage of the source rises or drops in the direction of one of the supply voltages V+ (in the case of a positive rated current) or V− (in the case of a negative rated current), wherein the absolute value of the current Ia becomes small, i.e. approaches 0 mA. This behavior is illustrated in an exemplary fashion in FIGS. 3b and 3c, once for a positive rated current Ia_N and once for a negative rated current −IaN. If a positive current and then a negative current occurs at the power source SQ, in the case of a high or infinite resistance there is therefore a high output voltage and then a low output voltage, wherein in the case of a positive current a positive voltage is to be expected, and in the case of a negative current a negative voltage is to be expected.

Taking into account the behavior of real power sources in principle permits breaks in the lines which are connected to the first and the third terminal to be detected. However, it is not yet possible to detect here whether a break in the line which is connected to the third terminal VG (referred to as the VG line) is present. If the VG line is interrupted, the currents could still flow from one of the power sources SQ1 and SQ2, respectively, into the other power source SQ2 or SQ1 since there is still an electrical connection across the two cells NZ and PZ of the exhaust-gas sensor 10.

In order to detect an interrupted VG line, i.e. a line which is connected to the third terminal VG of the actuation circuit 20, symptoms are therefore used which occur when certain currents are set simultaneously in the power sources SQ1, SQ2 which are present:

1. In the power source SQ1, a positive current Icp is set in a first step. In addition, a positive current Icp is set at the power source SQ2. Both currents flow across the first and second terminal, VN and VIP, respectively, into the respective cells. Since the desired current cannot flow away at the terminal VG owing to the line break, Icp+Ip=0 must apply. According to the current/voltage characteristics, explained in conjunction with FIG. 2, of the power sources, SQ1, SQ2, high voltages must respectively occur at the terminals VN and VIP. Depending on how high the Nernst voltage Vn and the pumping cell voltage Vp are, different voltages occur at the terminals VN and VG. This relationship is illustrated schematically in FIG. 4.

Figure 4A:
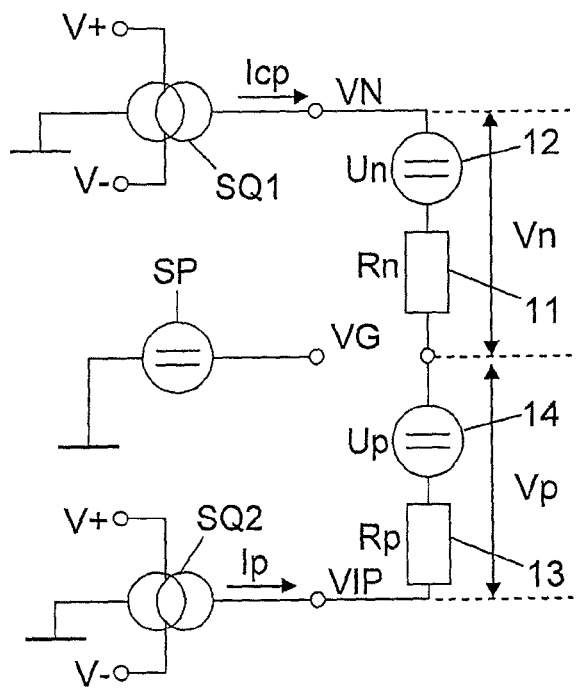

FIG. 4a shows the electrical equivalent circuit diagram of the actuation circuit 20 and of the exhaust-gas sensor 10 when there is an interrupted line to the third terminal VG.

Figure 4B:
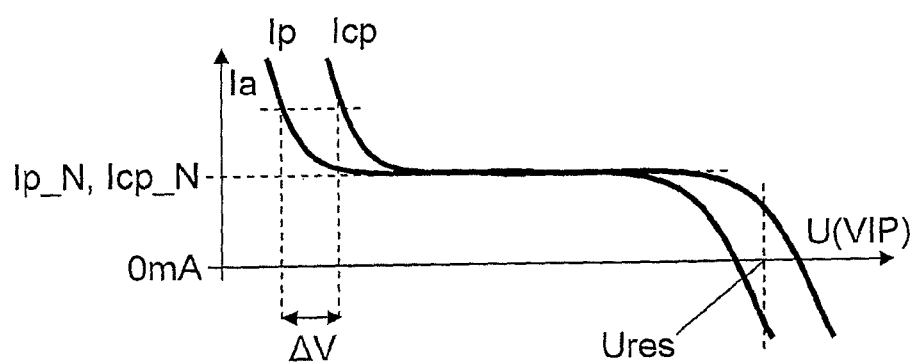

FIG. 4b shows the currents Icp and Ip, in each case plotted against the voltage U(VIP) present at the third terminal VIP. The expected rated current of the currents Icp and Ip in a fault-free case are specified by Icp_N and respectively Ip_N. The current/voltage curve of the first current Icp is shifted in this case by the sum of the cell voltages Vn and Vp compared to a diagram plotted against the voltage U(VN) present at the first terminal. This shift is denoted by ΔV in the figure. The resulting voltage Ures which occurs at the third terminal VIP is determined from the current/voltage characteristic curves of the sources SQ1 and SQ2 by the condition Icp+Ip=0. This means that in the case of Ures, the currents Icp and Ip are of equal size in absolute terms, but have different signs.

2. In the subsequent step, negative currents Icp and Ip are set. Since the condition Icp+Ip=0 has to apply again, low voltages occur. The determination of the resulting voltage Ures is carried out in a way analogous to the procedure described in conjunction with FIG. 4.

3. In a subsequent step, a positive, first current Icp and a negative circuit second current Ip are set. The second current Ip is in this case higher than the first current Icp in terms of absolute value. The resulting voltage Ures at the first terminal VN and at the second terminal VIP is relatively low corresponding to the expected behavior of the real power source.

Figure 5A:
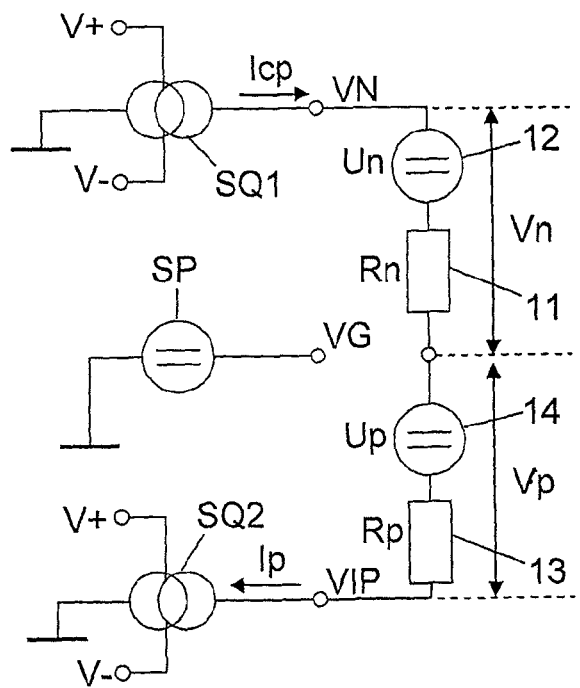

This situation is apparent from FIG. 5, wherein FIG. 5a shows the electrical equivalent circuit diagram of the exhaust-gas sensor 10 which is connected to the actuator circuit 20. The currents Icp and Ip are illustrated here in the correct direction corresponding to their sign. At the third terminal VG, the line is interrupted in accordance with the assumption.

Figure 5B:
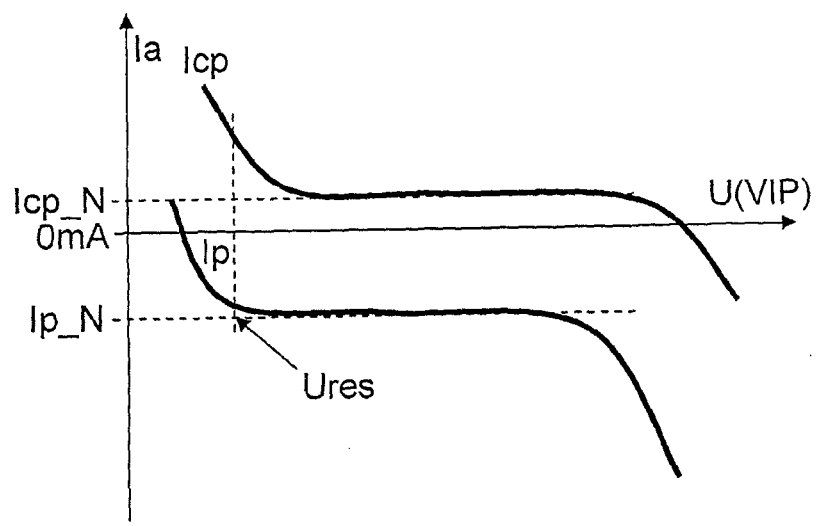

FIG. 5b shows the profile of the currents Icp and Ip plotted against the voltage U(VIP) present at the third terminal VIP. The current Icp is in turn shifted by the sum of the cell voltages Vn+Vp with respect to a diagram plotted against the voltage U(VN) present at the first terminal VN. Since the condition Icp+Ip=0 has to be met again, the expected low voltage Ures results, at which voltage the currents Icp and Ip are of equal size in absolute terms but have a different sign.

4. Finally, in a fourth step a negative first current Icp and a positive second current Ip are set. In absolute terms, the second current Ip is higher than the first current Icp. The resulting voltage at the first and second terminals VN and VIP is of an expected magnitude in accordance with the behavior of real power sources. This situation is illustrated in FIG. 6.

Figure 6A:
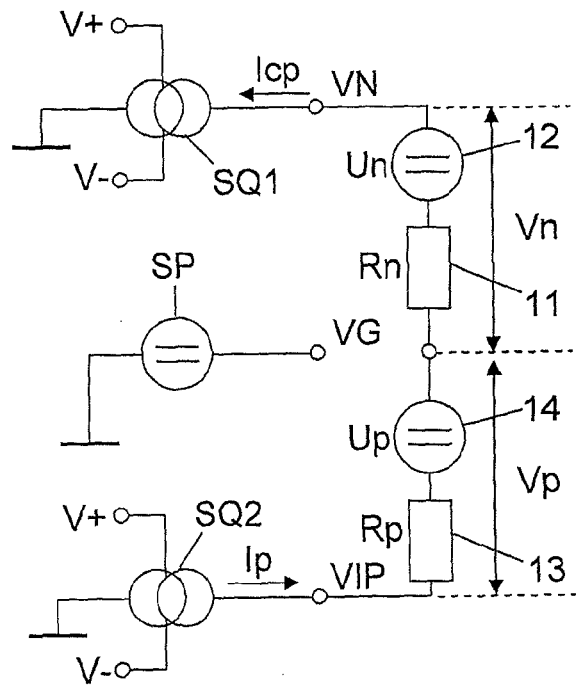

FIG. 6a in turn shows the electrical equivalent circuit diagram of the exhaust-gas sensor 10 which is connected to the actuation circuit 20. In this context, the currents Icp and Ip are shown correctly in accordance with their sign. The line is in turn interrupted at the terminal VG.

Figure 6B:
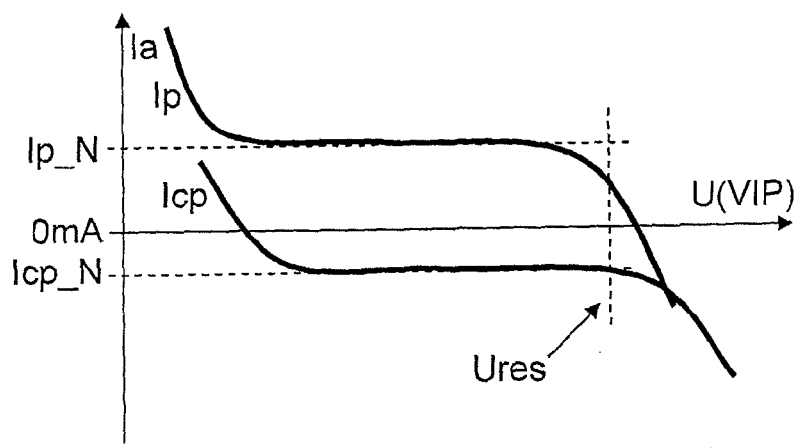

FIG. 6b shows the profile of the currents Icp and Ip plotted against the voltage U(VIP) which occurs at the third terminal VIP. The profile of the first current Icp is shifted by the sum of the cell voltages Vn+Vp compared to a diagram plotted against the voltage at the first terminal VN. The voltage which occurs at the third terminal VIP appears in turn owing to the conditions:

Icp+Ip=0 which is to be met. This condition is met in the case of a relatively high voltage U(VIP), cf. the voltage Ures which occurs.

In the preceding description, the currents Icp and Ip were plotted against the voltage U(VIP) which occurred at the third terminal VIP. Of course, the currents Icp and Ip could also be plotted against the voltage U(VN) which occurs at the first terminal VN, wherein the condition Icp+Ip=0 also has to be met. In a corresponding way, the shifting of the current/voltage characteristics of Ip and Icp owing to the sum of the cell voltages Vn+Vp must then also be taken into account.

In the first two steps 1 and 2, the voltages on the lines do not differ significantly from those in the case of a break in the respective line itself. However, in the steps 3 and 4, the behavior on the line with the set current which is lower in absolute terms, i.e. the line which is connected to the first terminal VN, is different. Where a high voltage is to be expected in the case of a break in the line itself, a low voltage is observed when there is a break in the line connected to the third terminal, and vice versa.

The following features are therefore used to detect a break in the line which is connected to the third terminal VG: the voltages at the terminals VN and VG in the case of positive Ip currents and Icp currents; the voltages at the terminals VN and VG in the case of negative Icp and Ip currents. The voltages at the terminals VN and VG in the case of positive Ip currents and negative Icp currents; the voltages at the terminals VN and VG in the case of a negative Ip current and positive Icp current. In accordance with the preceding illustration, the currents Ip and Icp are coordinated and the voltage measurements at at least one of the terminals VN and VG are related thereto. This procedure is illustrated in exemplary fashion in a matrix in FIG. 7.

Figure 7:
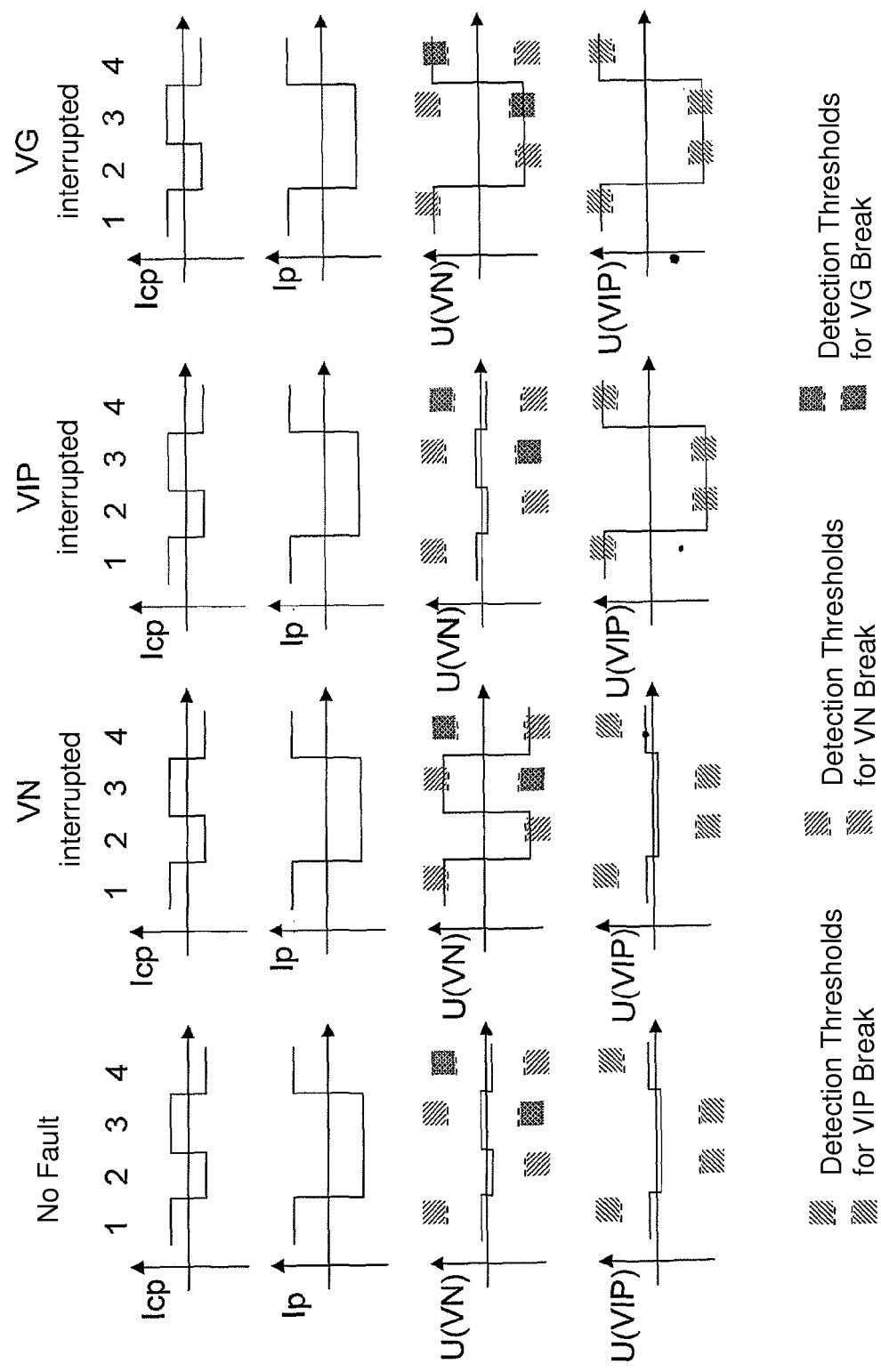
FIG. 7 shows the current profiles and voltage profiles at the first and second terminal of the diagnostic circuits in different operating states.

FIG. 7 shows the voltage profiles U(VN) at the first terminal VN and U(VIP) at the second terminal VIP as a function of the currents Icp and Ip. For the described steps 1, 2, 3 and 4, the voltages which respectively occur at the terminals VN and VIP are illustrated for the cases "no fault", "VN interrupted" (i.e. the line connected to the terminal VN is interrupted), "VIP interrupted" (i.e. the line connected to the terminal VIP is interrupted) and "VG interrupted" (i.e. the line which is connected to the terminal VG is interrupted). 1, 2, 3 and 4 detection thresholds are respectively shown for the steps in the diagrams of the voltage profiles U(VN) and U(VIP). The respective detection thresholds are illustrated by horizontal, dashed lines. The detection threshold for the break at the terminal VIP is characterized by hatching from bottom left to top right. The detection threshold for a break at the terminal VN is characterized by hatching from top left to bottom right. The detection threshold for the break at the terminal VG is characterized by intersecting, diagonally extending lines.

While in the case "no faults" none of the thresholds is exceeded by one of the voltages U(VN) or U(VIP), in the case "VN interrupted" the thresholds are exceeded at the terminal VN in all the steps 1 to 4. In contrast, the voltage U(VIP) at the terminal VIP behaves in an unsurprising way.

If the line at the terminal VIP is interrupted, the voltage U(VN) at the terminal VN is normal, while the voltage U(VIP) at the terminal VIP exceeds the respective detection threshold in all the steps 1, 2, 3 and 4.

If a line is interrupted at the terminal VG, the voltage at the terminal VIP behaves in accordance with a break in the line at the terminal VIP. However, atypical behavior of the voltage U(VN) can be found to occur at the terminal VN, wherein the predefined detection thresholds are exceeded in particular in the steps 3 and 4 in which the currents Icp and Ip have different signs.

The diagnosis can be configured particularly easily if a measurement of the internal resistance is implemented in the actuation circuit and the results of said measurement are also used for the diagnosis of the exhaust-gas sensor. The measurement of the internal resistance applies an alternating current to the Nernst cell NZ. This means that positive and negative Icp currents are generated by the alternating-current power source SQ1. A signal fault which is connected to the Nernst cell determines the resulting amplitude of the Nernst cell voltage Vn. This is done by forming the difference between the voltages at the terminal VN which occur in the case of a positive Icp current and in the case of a negative Icp current. In addition, the signal filter forms the mean value of the Nernst cell voltage Vn.

This procedure is illustrated schematically in FIG. 8a, wherein the square-wave profile of the current Icp plotted over time and the profile of the voltage U(VN) at the terminal VN plotted over time are illustrated. The positive and negative amplitudes of the voltage U(VN) at the terminal VN are respectively characterized by Vn+ and Vn−. As part of the measurement of the internal resistance, measurement is carried out in a synchronized fashion with the "Icp alternating current" Vn+ in the case of a positive cell current and Vn− in the case of a negative cell current. The amplitude Vn_AC of the voltage which is present at the terminal Vn results from the difference between Vn+ and Vn− and is usually positive. The mean value Vn_DC is calculated as follows: Vn_DC=(Vn++Vn−)/2. The amplitude Vp_AC and the mean value Vp_DC of the pumping cell voltage Vp are determined in an analogous fashion.

The measured values which are available can be used to create a matrix for detecting electrical faults in the case of in phase and anti-phase Ip currents and Icp currents:

| Fault | Vn_AC (phase 1) | Vn_AC (phase 2) | Vp_AC (phase 1) | Vp_AC (phase 2) | Vn_DC | Vp_DC |
|---|---|---|---|---|---|---|
| No | <max-limit | <max-limit >min-limit | <max-limit | <max-limit | >min-limit <max-limit | >min-limit <max-limit |
| VN open (VG cannot be detected) | >max-limit | >max-limit >min-limit | <max-limit | <max-limit | >min-limit <max-limit | >min-limit <max-limit |
| VIP open (VG cannot be detected | <max-limit | <max-limit >min-limit | >0 >max-limit | >0 >max-limit | >min-limit <max-limit | >min-limit <max-limit |
| VG open and VIP open (VG cannot be detected) | >max-limit | >max-limit >min-limit | >0 >max-limit | >0 >max-limit | >min-limit <max-limit | >min-limit <max-limit |
| VG open VN and VIP ok) | >max-limit | <max-limit <min-limit | >0 >max-limit | >0 >max-limit | >min-limit <max-limit | >min-limit <max-limit |
| VN short circuit battery | <max-limit | <max-limit >min-limit | <max-limit | <max-limit | >min-limit <max-limit | >min-limit <max-limit |
| VN short circuit ground | <max-limit | <max-limit >min-limit | <max-limit | <max-limit | <min-limit <max-limit | min-limit <max-limit |
| VIP short circuit battery | <max-limit | <max-limit >min-limit | <max-limit | <max-limit | >min-limit max-limit | >min-limit >max-limit |
| VIP short circuit ground | <max-limit | <max-limit >min-limit | <max-limit | <max-limit | min-limit <max-limit | <min-limit <max-limit |

Various detectable faults are illustrated in the matrix, wherein the conditions which have to be respectively met have to be met for Vn_AC in phase 1, Vn_AC in phase 2, Vp_AC in phase 1, Vp_AC in phase 2, Vn_DC and Vp_DC. max limit characterizes an upper, detected limit, and mit-limit characterizes a lower, monitored limit. If two conditions (limits) are specified in a respective table entry, they both have to be met simultaneously. The behavior of the voltages at the terminals VN and VIP is checked in each case with currents Icp and Ip applied in a coordinated fashion.

Phase 1 is characterized in that Icp and Ip are in phase (cf. FIG. 8b). In phase 2, Icp and Ip are in anti-phase (cf. FIG. 8c). The voltage profile which occurs at the terminals VN and VIP and the conditions which apply in the case of a break in the lines connected to the terminal VG are also illustrated.

The diagnostics require specific currents to be applied to the Nernst cell NZ and pumping cell PZ of the exhaust-gas sensor 10. The diagnostics therefore require the normally active pumping current control to be switched off. This leads to a situation in which no lambda measurement is temporary possible during the diagnostics.

This is generally not critical since the theoretical presence of a line fault as a matter of principle gives rise to typical known symptoms. For example, an excessively high internal resistance is measured or the pumping current controller runs to an end position. The diagnostics must therefore be carried out only if a fault has been detected in any case and said fault has to be determined more precisely.

The diagnostic circuit which carries out the diagnostics is not explicitly illustrated in the schematic figures. The diagnostic circuit is part of the actuation circuit 20 and is designed to carry out the voltage measurements which are necessary for the diagnostics described above and to relate said voltage measurements to the currents applied by the power sources SQ1 and SQ2.

The invention claimed is:

1. A device for diagnosing an exhaust gas sensor, comprising:
   a first connection for connecting to a first electrode of a first cell of the exhaust gas sensor;
   a second connection for connecting to a second electrode of a second cell of the exhaust gas sensor,
   a third connection for connecting to a node of a second electrode of the first cell and a first electrode of the second cell of the exhaust gas sensor,
   a first power source which is coupled to the first connection, in order to generate a first current and impress the first current into the first cell, a second power source which is coupled to the second connection, in order to generate a second current and impress the second current into the second cell, and
   a diagnostic means for detecting a break in a line at at least one connection selected from the group consisting of the first connection, the second connection, and the third connection, said diagnostic means designed to control the first and second power sources and to take measurements in all of the following cases:
   (a) to control the first power source to generate the first current with a positive sign and to control the second power source to generate the second current with a positive skin while detecting voltages at the first and second connections,
   (b) to control the first power source to generate the first current with a negative sign and to control the second power source to generate the second current with a negative sign while detecting voltages at the first and second connections,
   (c) to control the first power source to generate the first current with a negative sign and a smaller absolute value than the second current and to control the second power source to generate the second current with a negative skin while detecting voltages at the first and second connections, and
   (d) to control the first power source to generate the first current with a negative sign and a smaller absolute value than the second current and to control the second power source to generate the second current with a positive skin while detecting voltages at the first and second connections;
   said diagnostic means designed to detect a line break at the third connection when performing the case (c) and detecting that the voltages at the first and second connections are each below a predefined negative threshold value; and
   said diagnostic means designed to detect a line break at the third connection when performing the case (d) and detecting that the voltages at the first and second connections are each above a predefined positive threshold value.

2. The device according to claim 1, in which said diagnostic means is designed to detect a line break at the first connection upon detecting a voltage above a predefined positive threshold value at the first connection in the cases (a) and (c) and upon detecting a voltage below a predefined negative threshold value at the first connection in the cases (b) and (d).

3. The device according to claim 1, wherein said diagnostic means is designed to detect a line break at the second connection upon detecting a voltage above a predefined positive threshold value at the second connection in the cases (a) and (d) and upon detecting a voltage below a predefined negative threshold value at the second connection in the cases (b) and (c).

4. The device according to claim 1, wherein said diagnostic means includes a first signal filter, and said first signal filter is connected and configured in a manner selected from the group consisting of:
said first signal filter is connected to the first and third connections, and said first signal filter is configured to determine a first amplitude that results from the first current of a cell voltage of the first cell; and
said first signal filter is connected to the second and third connections, and said first signal filter is configured to determine a second amplitude that results from the second current of a cell voltage of the second cell.

5. The device as claimed in claim 4, wherein the first signal filter is switchable between the first and third connections and the second and third connections.

6. The device as claimed in claim 4, wherein said diagnostic means includes a first computing unit for determining a mean value of the cell voltage of the first cell.

7. The device according to claim 4, wherein said diagnostic means includes a second signal filter which is connected to the second and third connections and by which a second amplitude of the cell voltage, resulting from the second current, of the second cell can be determined.

8. The device according to claim 4, wherein said diagnostic means includes a second computing unit for determining a mean value of the cell voltage of the second cell.

9. The device according to claim 1, wherein the first power source is an alternating power source for measuring an internal resistance of the first cell.

10. The device according to claim 1, wherein the second power source is a pumping power source or is embodied as a separate power source.

11. A method for diagnosing an exhaust gas sensor, which comprises:
providing a device that includes:
a first connection for connecting to a first electrode of a first cell of the exhaust gas sensor,
a second connection for connecting to a second electrode of a second cell of the exhaust gas sensor,
a third connection for connecting to a node of a second electrode of the first cell and a first electrode of the second cell of the exhaust gas sensor,
a first power source which is coupled to the first connection in order to generate a first current and to impress the first current into the first cell,
a second power source which is coupled to the second connection in order to generate a second current and impress the second current into the second cell, and
a diagnostic means for detecting a line break at at least one connection selected from the group consisting of the first connection, the second connection, and the third connection,
wherein the diagnostic means is designed to control the first and second power sources and to take measurements in all of the following cases:
(a) to control the first power source to generate the first current with a positive sign and to control the second power source to generate the second current with a positive skin while detecting voltages at the first and second connections,
(b) to control the first power source to generate the first current with a negative sign and to control the second power source to generate the second current with a negative sign while detecting voltages at the first and second connections,
(c) to control the first power source to generate the first current with a negative sign and a smaller absolute value than the second current and to control the second power source to generate the second current with a negative sign while detecting voltages at the first and second connections, and
(d) to control the first power source to generate the first current with a negative sign and a smaller absolute value than the second current and to control the second power source to generate the second current with a positive sign while detecting voltages at the first and second connections;
said diagnostic means designed to detect a line break at the third connection when performing the case (c) and detecting that the voltages at the first and second connections are each below a predefined negative threshold value; and
said diagnostic means designed to detect a line break at the third connection when performing the case (d) and detecting that the voltages at the first and second connections are each above a predefined positive threshold value.

12. The method according to claim 11, wherein a line break is detected at the first connection upon detecting a voltage above a predefined positive threshold value at the first connection in the cases (a) and (c) and upon detecting a voltage below a predefined negative threshold value at the first connection in the cases (b) and (d).

13. The method according to claim 11, wherein a line break is detected at the second connection upon detecting a voltage above a predefined positive threshold value at the second connection in the cases (a) and (d) and upon detecting a voltage below a predefined negative threshold value at the second connection in the cases (b) and (c).

14. The method according to claim 11, wherein the exhaust gas sensor is a linear oxygen probe for an internal combustion engine.

* * * * *